United States Patent
Olstowski (10) Patent No.: US 7,381,973 B2
(45) Date of Patent: *Jun. 3, 2008

(54) ANALYZER SYSTEM AND METHOD INCORPORATING EXCIMER UV FLUORESCENCE DETECTION

(76) Inventor: Franek Olstowski, 4010 Cedar Gardens, Houston, TX (US) 77082

(*) Notice: Subject to any disclaimer, the term of this patent is extended or adjusted under 35 U.S.C. 154(b) by 0 days.

This patent is subject to a terminal disclaimer.

(21) Appl. No.: 11/825,244

(22) Filed: Jul. 5, 2007

(65) Prior Publication Data

US 2007/0257203 A1    Nov. 8, 2007

Related U.S. Application Data

(62) Division of application No. 10/330,414, filed on Dec. 27, 2002, now Pat. No. 7,268,355.

(51) Int. Cl.
    G01N 21/64    (2006.01)
(52) U.S. Cl. .................. 250/461.1; 250/458.1; 250/459.1
(58) Field of Classification Search .......... 250/458.1, 250/459.1, 461.1; 356/417
    See application file for complete search history.

(56) References Cited

U.S. PATENT DOCUMENTS

| | | | |
|---|---|---|---|
| 4,469,946 A | | 9/1984 | Tanaka et al. |
| 4,710,679 A | * | 12/1987 | Budinger et al. ............ 315/58 |
| 4,837,484 A | | 6/1989 | Eliasson et al. |
| 5,504,391 A | | 4/1996 | Turner et al. |

(Continued)

OTHER PUBLICATIONS

Okabe, H., Fluorescence & Predissociation of Sulfur Dioxide, Dec. 15, 1971, 7095-7096, 93:25 J. Am. Chem. Soc. Note Previously Submitted.

(Continued)

Primary Examiner—David Porta
Assistant Examiner—Mark R Gaworecki
(74) Attorney, Agent, or Firm—Alton W. Payne (57) ABSTRACT

A system for measuring the amount of sulfur in a sample is provided comprising a UV fluorescence detector for determining the sulfur dioxide content of the sample and an analyzer for receiving the sulfur dioxide content of the sample from the UV fluorescence detector for evaluating the content of species under investigation and for quantifying the sulfur content in the sample. The UV fluorescence detector comprising an excimer lamp comprising a quartz envelope and a krypton-chloride excimer gas mixture therein. The quartz envelope comprising the emission aperture substantially perpendicular to the longitudinal axis of the quartz envelope for transmitting photons there through, an inner electrode comprising a conductive solid metallic rod having effective contact with the interior cylindrical surface of the quartz envelope, and an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode. Further, the outer electrode may comprise a first member and a second member symmetrically divided along the longitudinal axis of the quartz envelope, such that when the two members are joined together to encapsulate and hold the quartz envelope there between with an interior diameter closely coinciding with the outer diameter of the quartz envelope. In another embodiment of the present invention, a UV fluorescence method for determining the sulfur dioxide content of a sample is provided.

8 Claims, 4 Drawing Sheets

U.S. PATENT DOCUMENTS

| | | | |
|---|---|---|---|
| 5,510,158 | A | 4/1996 | Hiramoto |
| 6,133,694 | A | 10/2000 | Cekic |
| 6,342,702 | B1 | 1/2002 | Jinbo |
| 6,379,024 | B1 | 4/2002 | Kogure |
| 6,407,383 | B1 | 6/2002 | Byatt |
| 6,525,472 | B2 | 2/2003 | Okugi |
| 6,734,629 | B2 | 5/2004 | Arnold |
| 6,828,568 | B2 | 12/2004 | Suzuki et al. |

OTHER PUBLICATIONS

Okabe, H., Fluorescence Quenching of Sulfur Dioxide by Source Emission Gases, Sep. 1976, 487-1489, V.48, No. 11.

Schwarz, F.P., Okabe, H. & Whittaker, J.K., Fluorescence Detection of Sulfur Dioxide in Air at the Parts per Billion Level, Jul. 1974, 1024-1027, vol. 46, No. 8.

Bradshaw,J.D., Rodgers,M.O., and Davis,D.D., Single photon laser-induced fluorescence detection of NO and SO2 for atmospheric Conditions . . . , Jul. 15, 1982, 2493-2500, V.21, No. 14.

Mattee, H.D., Fluoresence & Phosphorescence of SO2 Vapor, Aug. 15, 1968, J.ChemPhy., vol. 49, No. 4.

Mohn, J. & L. Emmenegger, Determination of Sulfer Doixide by Pulsed UV-Fluorescence, 2001, Swiss Federal Laboritories for Materials Testing & Research.

Murray, J.R. & H.T. Powell, KrCl Laser Oscillation at 222nm, Aug. 15, 1976, Applied Phy. Letters, vol. 29, No. 4.

Uchino, Maeda & Hirono, Applications of Excimer Lasers to Laser-Radar Observations of the Upper Atmosphere, Oct. 1979, IEEE J.Quantum Elec., vol. QE-15, No. 10.

Kogelschatz, U., Fundamentals & Applications of Dielectric-Barrier Discharges, May 24, 2000, ABB Corporate Research Ltd., Baden, Switzerland.

Brashears, Setser & Yu, Emission Spectra of KrXeCl, KrXeBr, KrXeI, ArKrF & ArKrCl, Jan. 1, 1981, J. Chem. Phys., vol. 74, No. 1.

Zhang & Boyd, Efficient excimer ultraviolet sources from a dielectric barrier discharge in rare-gas/halogen mixtures, Apr. 9, 1996, J. Appl. Phys., vol. 80, No. 2.

Kogelschatz, Ulrich, Silent discharges for the generation of ultraviolet & vacuum ultraviolet excimer radiation, 1990, Pure & Appld. Chem., vol. 62, No. 9.

Burgard, Dalton, et al., Nitrogen dioxide, sulfur dioxide, and ammonia detector for remote sensing of vehicle emissions, 2006, Rev. Sci. Instrum., vol. 77, p. 014101-1 to -5.

Kelly Chance, Ultraviolet & visible spectroscopy & spaceborne remote sensing of the Earth's atmosphere, 2005, R.C. Physique, vol. 6, pp. 836-847.

Harry V. Drushel, Trace Sulfer Determination in Petroleum Fractions, 1978, Analytical Chemistry, vol. 50, No. 1, pp. 76-81.

M.V. Erofeev, et al., Miniture KrCl & XeBr Excimer Lamps, 2003, J. Applied Spectroscopy, vol. 70, No. 5, pp. 807-810.

Xiangfen Feng, et al., Investigation of excimer ultraviolet sources from dielectric barrier discharge in krypton & halogen mixtures, 2006, Physica Scripta, vol. 74, pp. 322-325.

K.F. Greenough et al., The Fluorescence of Sulfur Dioxide, Feb. 5, 1961, vol. 83, pp. 555-560.

E. Hegazi et al., Fluorescence of Indirectly Excited Low Vibrational Levels of the 1A2 State of Sulfur Dioxide, 1994, J.Phys.Chem., vol. 98, pp. 12169-12175.

M. Heymann et al., UV Absorption Study of Collisional Energy Transfer In Vibrationally High Excited SO2 Molecules, 1988, J.Phys.Chem., vol. 92, pp. 5507-5514.

H. Hippler et al., Excitation Dependence of the Ultraviolet Absorption Spectrum of SO2, 1988, J.Phys.Chem., vol. 92, pp. 5503-5506.

U. Kogelschatz et al., High Intensity sources of ibcoherent UV &VUV excimer radiation for low-temperature materials processing, 2000, Applied Surface Sci., vol. 168, pp. 29-36.

J.P. Koplow et al., Development of a narrow-band, tunable, frequency-quadrupled diode laser for UV absorption spectroscopy, 1998, Applied Optice, vol. 37, No. 18, pp. 3954-3960.

D.C. Lorents et al., Optical emissions of triatomic rare gas halides, 1978, J.Phys.Chem., vol. 68, No. 10, pp. 4657-4661.

G.W. Luther III et al., Preface: Historical Background, 1997, J. Geophysical Research, vol. 102, No. D13, pp. 16,215-16,217.

R.A.Kishore Nadkarni, Determination of sulfur in petroleum products & lubricants: A critical review of test performance, 2000, American Laboratory, Nov., pp. 16,18,20,21-25.

T.N. Rao et al., The quenching reactions of the 1st excited singlet & triplet states of sulfur dioxide w/ O & CO2, 1969, J.Am.Chem. Soc., vol. 91, No. 7, p. 1616.

H.C.Brashears et al., Comm to the Editor, reactions of the Xe(3P1) & Kr(3P1) resonance states w/ halogen donor molecules, 1980, J.Phys.Chem., vol. 84, pp. 224-226.

J.H. Koltz et al., Reactive quenching studies of Xe(6s,3P2) metastable atoms by clorine containing molecules, 1979, J.Chem.Phys., vol. 71, No. 3, pp. 1247-1263.

J.E. Velazco et al., Rate constants and quenching mechanisms for the metastable states of argon, krypton and xenon, 1978, J.Chem. Phys., vol. 69, No. 10, pp. 4357-4371.

J.E. Velazco et al., Bound-free emission spectra of diatomic xenon halides, 1975, J.Chem.Phys., vol. 62, No. 5, pp. 1990-1991.

J.E. Velazco et al., Quenching rate constants for metastable argon, krypton, & xenon atoms by fluorine containing molecules . . . , 1976, J.Chem.Phys., vol. 65, No. 9, pp. 3468-3480.

\* cited by examiner

FIG. 5

ANALYZER SYSTEM AND METHOD INCORPORATING EXCIMER UV FLUORESCENCE DETECTION

CROSS REFERENCE TO RELATED APPLICATION

The present application is a divisional application of the application of Franek Olstowski, U.S. Ser. No. 10/330,414, filed Dec. 27, 2002, now U.S. Pat. No. 7,268,355 entitled EXCIMER UV FLUORESCENCE DETECTION.

FIELD OF THE INVENTION

The present invention relates to a system and method for excimer UV fluorescence detection. More specifically, the present invention provides a system and method for enhancing the detection of sulfur dioxide using ultraviolet fluorescence. And even more specifically, the present invention provides a system and method for detecting sulfur dioxide using a KrCl dielectric barrier-discharge (DBD) excimer lamp.

BACKGROUND OF THE INVENTION

Efforts to reduce the environmental impact resulting from combustion of hydrocarbon fuels continues to place increasingly stringent requirements on acceptable levels of total bound sulfur content in motor fuels. Recently issued federally mandated guidelines will eventually pose a significant challenge to present ASTM methods for laboratory and on-line analysis of these products with desired concentrations even lower than presently imposed. As a result, improved or alternative methods need to be developed in order to keep pace with strict requirements being placed on these fuels. The following describes a proposed improved method and the associated predictive results.

At present, the X-Ray Fluorescence (XRF) method has limited ability to provide repeatable analysis of sulfur content below present guidelines. Flame Photometric Detection (FPD) and Sulfur Chemiluminescence (SCD) methods possess much greater sensitivity, but suffer from a variety of problems. Both methods require the use of hydrogen, a hazardous gas, which increases the cost and complexity of these systems in order to meet safety requirements. The FPD method also has a characteristic non-linear response to sulfur requiring multi-point calibration and/or sulfur addition to approximate linear results. Chemiluminescence analysis additionally requires a stable vacuum source and ozone generator, increasing system complexity and making it notorious for high maintenance and long-term stability issues.

The simplest, most practical low-level sulfur analysis technique that has been widely used and proven over many years of utilization is the UV Fluorescence method. This method involves the optical excitation of sulfur dioxide and detecting a longer wavelength, secondary emission continuum. Total sulfur content in fuels is determined by complete combustion of all hydrocarbon and sulfur species, which are oxidized to $CO_2$, $H_2O$ and $SO_2$.

Originally developed UV fluorescence detectors were continuous types, but sensitivity of these detectors is somewhat limited due to inherent background noise or baseline instability, which is partially due to lamp intensity variations from plasma instabilities within the UV excitation lamp. Both cadmium and zinc excitation lamps have been successfully applied utilizing the 228 nm and 214 nm emission lines respectively, but the present accepted ASTM method favors the zinc lamp due to minimal fluorescence quenching influence from variations in the moisture content of the sample.

In an attempt to further decrease lower detectable limits, the Pulsed UV Fluorescence (PUVF) method was developed. The operating principle of PUVF is very similar to continuous type UV Fluorescence detectors, except that it uses a xenon flashlamp as the excitation source. Since the light is electronically "pulsed," signal-to-noise ratios are improved and a lower level of detectability can be routinely achieved. However, since flashlamp intensity varies substantially from pulse-to-pulse, flash intensity is electronically normalized utilizing a separate light detector and induced fluorescence is averaged over a period of time. The PUVF detector is ideally suited for atmospheric monitoring and similar type applications where typically encountered $SO_2$ concentrations generally change more slowly with time. Unfortunately, the pulsing excitation source also renders the PUVF a poor detector for higher speed detection requirements, such as total sulfur peak integration or sulfur speciation applications by chromatographic analysis.

In addition, the complexity of additional electronics required for flashlamp operation, signal synchronization and subsequent data averaging yields a detector that is considerably more complex and costs more than the continuous type UV detectors.

Although some additional improvement to accepted UV fluorescence detection methods may be realized by optimizing detector design, inherent limitations prevent the present methods from any quantum increase in sensitivity. Most efforts to further enhance sensitivity are primarily applied to reduction of background noise through improved detector geometry and careful selection of optical components to maximize excitation and fluorescence signals. Since several manufacturers of $SO_2$ fluorescence detectors have attempted to push the limits of detection for many years, it is this author's opinion that significant improvement to present detection levels is unlikely utilizing present methods.

There exists, therefore, a need for improved UV fluorescence detection of sulfur dioxide having enhanced sensitivity.

A new excitation source can yield a significant improvement to present $SO_2$ sensitivities achieved with ASTM accepted standards utilizing UV Fluorescence methods. This new excitation source, or Excimer lamp, creates a high intensity UV emission that possesses higher spectral purity than traditional zinc or cadmium lamps.

Excimer lamps are barrier-discharge devices based on the "excited dimer" principle and contain either an inert fill gas or a specific halogen and inert fill gas mixture. An alternating high voltage field is applied to electrodes separated by an insulating medium or dielectric and induces the generation of microscopic internal filament discharges, which excite fill gas atoms into briefly forming an excited molecular species. These short-lived transient molecules rapidly dissociate and release photons of specific wavelengths directly related to the quantum energy lost in the transition to ground state.

A feature of the present invention is to provide a UV fluorescence detection system and method having emission that is caused by excitation at a wavelength that correlates with absorption bands of the species under investigation.

A feature of the present invention is to provide a UV fluorescence detection system and method having an excitation wavelength that correlates with peak absorption bands of $SO_2$ which create maximum fluorescence intensity.

Another feature of the present invention is to provide a UV fluorescence detection system and method possessing maximum fluorescence intensity at or near an excitation wavelength of 222 nm so as to correlate with absorption bands that induce the greatest fluorescence emission.

Another feature of the present invention is to provide a UV fluorescence detection system and method utilizing a dielectric barrier-discharge excimer lamp.

Another feature of the present invention is to provide a UV fluorescence detection system and method utilizing a krypton-chloride (KrCl*) excimer mixture.

Another feature of the present invention is to provide a UV fluorescence detection system and method having an excitation source with higher spectral emission purity to decrease the effects of background measurement limitations.

Another feature of the present invention is to provide a UV fluorescence detection system and method having an excitation source with higher spectral emission purity so as to increase signal to noise ratio.

Yet another feature of the invention is to provide a UV fluorescence detection system and method having an excitation source with higher spectral purity so as to possibly eliminate the need for an excitation source filter for some applications.

Another feature of the present invention is to provide a UV fluorescence detection system and method that can be operated in either continuous or pulsed modes of operation.

Yet another feature of the present invention is to provide a pulsed UV fluorescence detection system and method for further lowering minimum detectable levels or concentrations.

Still another feature of the present invention is to produce $SO_2$ fluorescence with higher rejection ratios to interfering nitric oxide (NO) than obtained with a zinc lamp.

Yet another feature of the present invention is to provide a pulsed UV fluorescence detection system and method that can be closed-loop-feedback controlled for more stable operation.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a UV fluorescence detection system and method is provided.

In one embodiment of the present invention, a system for measuring the amount of sulfur in a sample is provided comprising a UV fluorescence detector for determining the sulfur dioxide content of the sample and an analyzer for receiving the sulfur dioxide content of the sample from the UV fluorescence detector for evaluating the content of species under investigation and for quantifying the sulfur content in the sample. The UV fluorescence detector comprising an excimer lamp comprising a quartz envelope and a krypton-chloride excimer gas mixture therein, an excitation source comprising the quartz envelope, a fluorescence chamber for housing a sample of gas containing sulfur dioxide such that the excitation source is in communication with the chamber and having a fluorescence emission filter, a light sensitive detector in operative association with the fluorescence filter of the fluorescence chamber, and a device in communication with the light sensitive detector for determining the sulfur dioxide content of the sample in the fluorescence chamber. The quartz envelope comprising an exterior cylindrical portion having an exterior cylindrical surface and an interior cylindrical surface, an interior cylindrical portion having an interior cylindrical surface and an exterior cylindrical surface, an emission aperture at a remote end of the quartz envelope in sealed association with the exterior cylindrical portion and the interior cylindrical portion, the emission aperture is substantially perpendicular to the longitudinal axis of the quartz envelope for transmitting photons there through, such that the interior cylindrical surface of the exterior cylindrical portion, the exterior cylindrical surface of the interior cylindrical portion and the emission aperture define a chamber for containing the krypton-chloride excimer gas mixture, an inner electrode comprising a conductive solid metallic rod having effective contact with the interior cylindrical surface of the quartz envelope, and an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode. Further, in one embodiment the outer electrode comprises a first member and a second member symmetrically divided along the longitudinal axis of the quartz envelope, such that when the two members are joined together to encapsulate and hold the quartz envelope there between with an interior diameter closely coinciding with the outer diameter of the quartz envelope.

In another embodiment of the present invention, a UV fluorescence method for determining the sulfur dioxide content of a sample is provided. The UV fluorescence method comprising the steps of detecting the sulfur dioxide content in the sample by exciting an excimer gas mixture within an excimer lamp, generating an emission spectrum by exciting the excimer gas mixture thereby, creating an optimal wavelength that enhances the fluorescence emission of sulfur dioxide, engaging the optimal wavelength with sulfur dioxide, generating an excited form of sulfur dioxide, inducing a fluorescence emission from the excited form of sulfur dioxide having a characteristic spectral profile specific to sulfur dioxide, and analyzing the emission from the characteristic spectral profile for evaluating the content of species under investigation and for quantifying the sulfur content in the sample.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

BRIEF DESCRIPTION OF THE DRAWINGS

The accompanying drawings which are incorporated in and constitute a part of the specification, illustrate preferred embodiments of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Excimer Lamp Operation

Excimer lamps generate high intensity, narrow band UV radiation through what is known as a dielectric barrier discharge and have also been referred to as silent discharge devices. Excimer lamps can have numerous configurations, but always contain two electrodes separated by at least one dielectric medium and a rare-gas or rare-gas-halogen mixture or complex. The dielectric medium most often used is a high purity quartz or fused-silica.

The operation of an excimer lamp begins when an alternating current, high-voltage field is applied to the electrodes. Since the dielectric medium will initially resist electrical current flow due to the highly resistive nature of all dielectric materials, a charge will begin to build between the electrodes. As the voltage or strength of the applied field continues to increase, a critical point known as dielectric breakdown is reached where the dielectric medium can no longer resist the increasing pressure of the applied field.

When the voltage reaches this point, electrical current will be transported through the dielectric and be transferred by a multitude of randomly distributed microscopic discharges into the excimer gas. The plasma created by these micro discharges ionizes the surrounding inert gas into an excited state. The excited rare-gas species will then transfer the loosely bound electron to the halogen molecule to form an "excited dimmer" or excimer complex. The excimer complex, sometimes referred to as an exciplex, is a molecular species whose induced formation does not allow it to exist in a ground state under normal conditions.

Due to the highly unstable nature of these exciplex molecules, their atoms will rapidly separate and decompose, usually within a few nanoseconds. During the process of molecular dissociation back to the ground state, their excitation energy is given up in the form of a UV photon. The wavelength of the emitted photon will depend on both the rare-gas or rare-gas-halogen species of the excimer complex and is directly related to the transitional energy lost between the excited and ground states of these molecules.

The typical emission spectrum of the KrCl* exciplex, displays a primary emission wavelength of 222 nm, although other much lower intensity wavelengths associated with similarly relevant excimer transitions are unavoidably present. The spectral distribution and level of relevant emission wavelengths has been found to be related to purity of the excimer gases, fill pressure and operating temperature.

UV Fluorescence Detector Operation

Once the photons leave the emission aperture of the lamp, they are collected by a lens, or pair of lenses made from an appropriate material for high UV transmission of the excimer wavelength. The function of the first lens is to collect and collimate expanding light rays emitted from the lamp. The second lens subsequently focuses the collimated light rays from the first lens to a focal point within the center of the fluorescence chamber and preferably directly in front of or normal to the light detector or photomultiplier axis.

Before the light enters a fluorescence chamber, it passes through a narrow band-pass interference filter. The function of this filter is to pass the desired excitation wavelength, in this case 222 nm, and reject or eliminate unwanted wavelengths from entering the chamber. Any wavelength other than the excitation wavelength can create an undesirable background that interferes with optimal fluorescence detection and particularly any wavelengths that fall within the fluorescence band of the excited or measured species.

The sample gas intended for measurement is directed to flow through the fluorescence or sample chamber. This gas may be atmospheric air or exhaust from an internal combustion engine that is drawn by vacuum pump or pressure, as might be the case for environmental monitoring or vehicle emission applications. Alternately, the sample could be exhaust from an oxidizing combustion furnace typically found in total sulfur analyzers for petroleum fuels and related products, as well as any unrelated sample that may contain $SO_2$, or other sulfur compounds that are converted to $SO_2$, for quantitative and/or qualitative analysis.

The energy from excitation light photons is absorbed by the $SO_2$ molecules which is then subsequently lost or degraded by various mechanisms. It can be re-emitted as radiation of the same wavelength in what is known as resonant fluorescence. Energy may also be lost in the form of heat as the net energy level decays to the lowest rotational or vibrational level within the same electronic singlet level.

The form of lost energy this detector is primarily intended to detect is most commonly referred to as just fluorescence, a phenomenon that occurs when $SO_2$ decays from the lowest rotational and vibrational level within the singlet levels back to the ground state. Fluorescence radiation contains less photon energy than the excitation source and is usually a broadband continuum of longer wavelengths. Fluorescence decay times are extremely fast, and for most practical purposes are considered near instantaneous.

However, such detectors additionally detect $SO_2$ phosphorescence, yet another form of radiated energy that takes place when a nonradiative transition first occurs as an excited singlet state molecule shifts to a corresponding triplet state before eventually decaying back to the ground state. Unlike fluorescence which has no significant persistence, phosphorescence is metastable and possesses a much lower probability of reverting back to the ground state resulting in an emission that lasts for measurably longer periods of time.

Since emission photons radiate equally in all directions, a relatively small fraction is collected by a second filter, known as the fluorescence filter. It is typically a broadband transmission filter that allows photons from fluorescence and phosphorescence emission of $SO_2$ to pass and possesses an ideal wavelength transmission range of approximately 250-450 nm.

The photons that pass through the fluorescence filter then impinge upon a light detector that should have reasonably high sensitivity to the fluorescence emission wavelengths. A detector commonly used for this type of application is a photomultiplier tube that utilizes a series of resistively coupled electrically charged plates, also called a "dynode chain," which converts photon energy to an electrical current. Once the $SO_2$ emission has been converted to an electrical representation, it can be processed by numerous analog and/or digital signal conditioning electronic configurations. These may include, but are not limited to signal filtration, peak detection, integration, data acquisition, signal averaging and statistical data analysis functions. Real-time and accumulated data may also be represented by a variety of measurement display configurations.

Operation

Reference will now be made in detail to the present preferred embodiments of the invention as described in the accompanying drawings.

Figure 1:
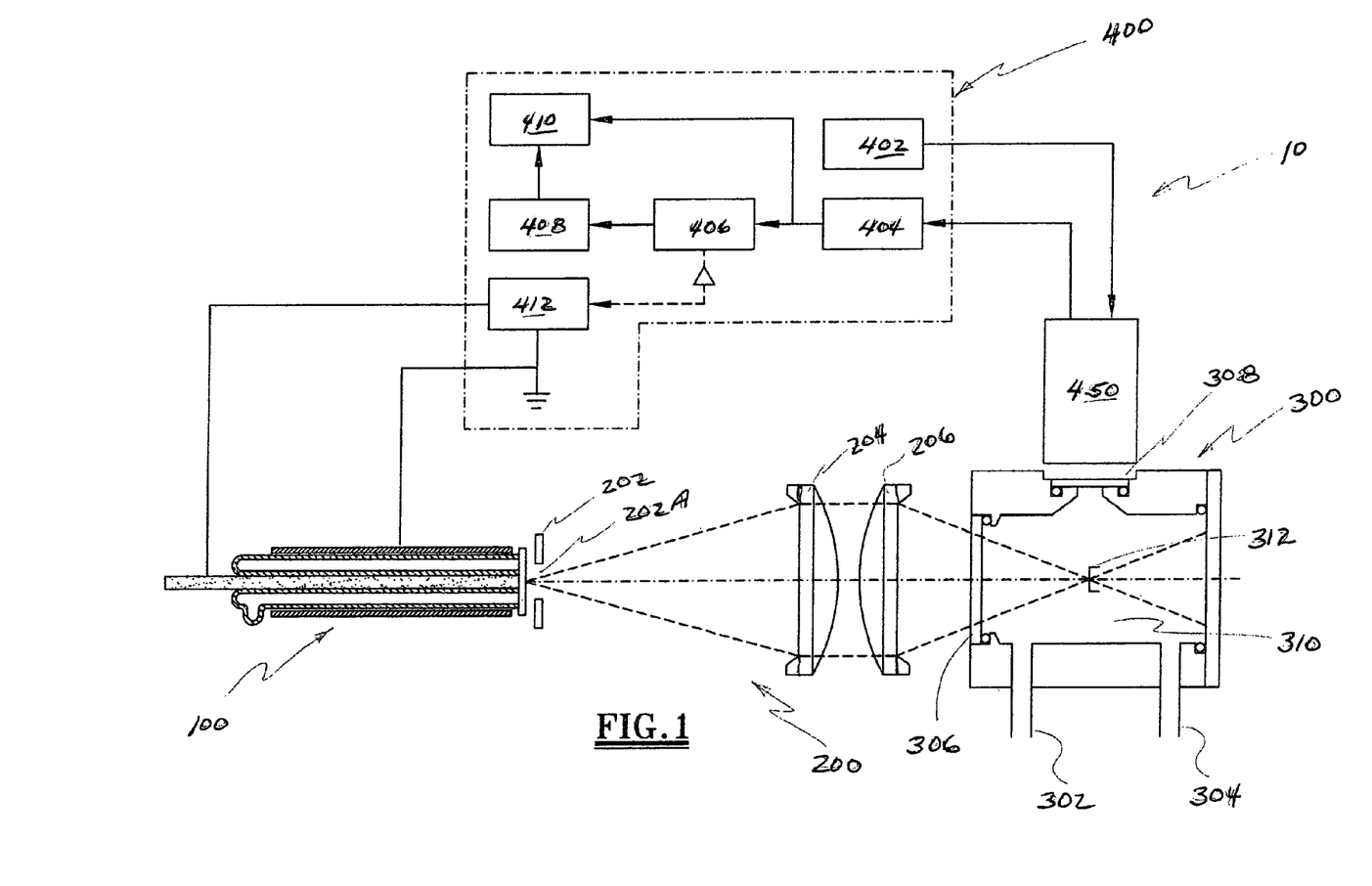
FIG. 1 is a schematic illustration of a preferred embodiment of the UV fluorescence detection system of the present invention.

FIG. 1 is a schematic illustration of a preferred embodiment of the UV fluorescence detection system 10 of the present invention. The primary components of the UV fluorescence detection system 10 are an excimer lamp 100, a light collection and lensing member 200, a fluorescence chamber 300 and an electronics/analysis member 400.

Figure 2:
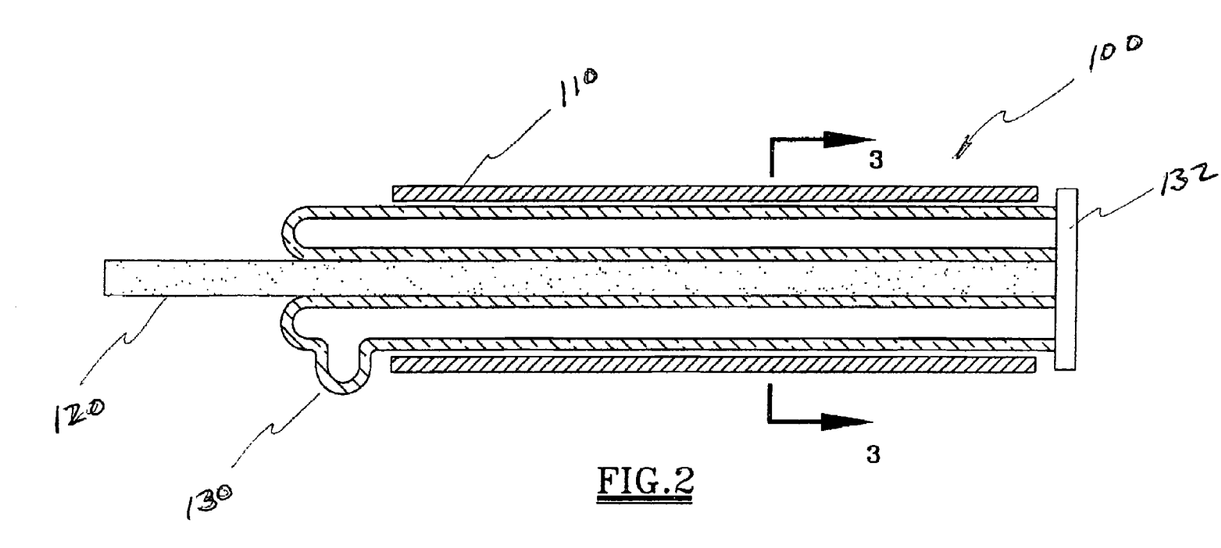
FIG. 2 is an exploded view of the excimer lamp illustrated in FIG. 1.
Figure 3:
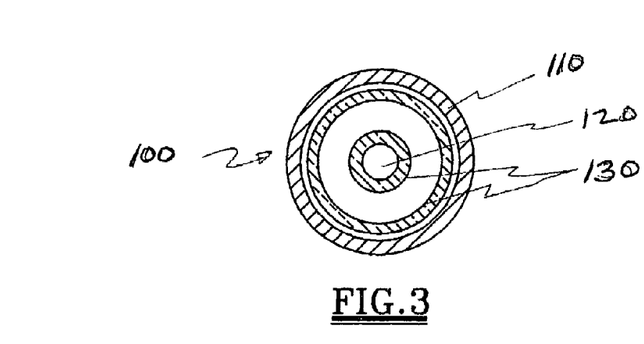
FIG. 3 is a cross section of the excimer lamp taken along the section 3-3 as illustrated in FIG. 2.

FIGS. 2 and 3 illustrated the details of the excimer lamp 100. It can be appreciated by the discussions above that the embodiment of the excimer lamp 100 can take many and numerous forms. The presently preferred embodiment of the excimer lamp 100 comprises an outer electrode 110, an inner electrode 120 and a quartz envelope 130. The quartz envelope 130 is bounded on an interior cylindrical surface by the inner electrode 120 and on an exterior cylindrical surface by the outer electrode 130.

The excimer lamp 100 is powered by the electronics 400. An alternating current, high-voltage field is applied to the electrodes 110, 120 of the excimer lamp 100 by the electronics 400. The dielectric medium will initially resist electrical current flow due to the highly resistive nature of the dielectric materials. A charge will begin to build between the electrodes 110, 120. As the voltage or strength of the applied field continues to increase, a critical point known as dielectric breakdown is reached.

When the voltage reaches the dielectric breakdown point, electrical current will conduct through the dielectric and be transferred by a number of randomly distributed microscopic discharges into the excimer gas within the quartz envelope 130. A plasma is created by the micro-discharges, which ionize the surrounding inert gas into an excited state. The excited rare-gas species will then transfer the loosely bound electron to the halogen molecule to form an "excited dimmer" or excimer complex. Due to the highly unstable nature of the exciplex molecules, their atoms will rapidly separate and decompose, usually within a few nanoseconds. During the process of molecular dissociation back to the ground state, their excitation energy is given up in the form of a UV photon. The wavelength of the emitted photon will depend on either the rare-gas or rare-gas-halogen species of the excimer complex within the quartz envelope 130 and is directly related to the transitional energy lost between the excited and ground states of the molecules.

The photons will leave the lamp 100 via the emission aperture 132. The emitted photons will pass through the lensing member 200 into the fluorescence chamber 300. In the lensing member 200, the photons will pass through an aperture 202A in an aperture member 202. Then, the photons are collected by a pair of lenses 204, 206 made from an appropriate material for high UV transmission of the excimer wavelength. The function of the first lens 204 is to collect and collimate expanding light rays emitted from the lamp 100. The second lens 206 subsequently focuses the collimated light rays from the first lens 204 to a focal point or foci 312 within the fluorescence chamber 300 and preferably directly in front of or normal to the light detector or photomultiplier 450.

Before the photons or light enters the fluorescence chamber 300, the photons pass through a narrow band-pass interference filter 306. The function of the narrow band-pass interference filter 306 is to pass the desired excitation wavelength, in this case 222 nm, and reject or eliminate unwanted wavelengths from entering the fluorescence chamber 300. Any wavelength other than the excitation wavelength can create an undesirable background that interferes with optimal fluorescence detection and particularly any wavelengths that fall within the fluorescence band of the excited or measured species, such as for example sulfur dioxide.

A sample gas intended for measurement is directed to flow through the fluorescence chamber 300 by entering via an inlet 302 traveling through the chamber 310 and exiting via an outlet 304. The sample gas may be, for example, atmospheric air or exhaust from an internal combustion engine that is drawn by vacuum pump or pressure, as might be the case for environmental monitoring or vehicle emission applications. Alternately, the sample could be exhaust from an oxidizing combustion furnace typically found in total sulfur analyzers for petroleum fuels and related products, as well as any unrelated sample that may contain $SO_2$, or other sulfur compounds that are converted to $SO_2$, for quantitative and/or qualitative analysis. The energy from excitation light photons is absorbed by the species under investigation, e.g. $SO_2$ molecules, which are then subsequently lost or degraded by various mechanisms. The energy can be re-emitted as radiation of the same wavelength in what is known as resonant fluorescence. Energy may also be lost in the form of heat as the net energy level decays to the lowest rotational or vibrational level within the same electronic singlet level. The detector 450 primarily detects fluorescence, a phenomenon that occurs when $SO_2$ decays from the lowest rotational and vibrational level within the singlet levels back to the ground state. However, it can be appreciated that other types of energy can be detected using the present invention. Such detectors additionally detect $SO_2$ phosphorescence, yet another form of radiated energy that takes place when a nonradiative transition occurs as an excited singlet state first shifts to a corresponding triplet state before eventually decaying back to the ground state. Unlike fluorescence which has no significant persistence, phosphorescence is metastable and possesses a much lower probability of reverting back to the ground state resulting in an emission that lasts for a measurably longer time period.

Emission photons radiate equally in all directions, and thus, a relatively small fraction are collected by a fluorescence filter 308 of the fluorescence chamber 300. The fluorescence filter 308 is typically a broadband transmission filter that allows photons from fluorescence and phosphorescence emission of the species under investigation to pass and possess an ideal wavelength transmission range, such as 250-450 nm for $SO_2$.

The photons that pass through the fluorescence filter 308 then impinge upon a light detector 450 that should have reasonably high sensitivity to the fluorescence emission wavelengths. A detector 450 commonly used for this type of application is a photomultiplier tube which converts photon energy to an electrical current. Once the $SO_2$ emission has been converted to an electrical representation, it can be processed by the electronics 400. The electronics 400 can be numerous analog and/or digital signal conditioning electronic configurations. These may include, but are not limited to signal filtration, peak detection, integration, data acquisition, signal averaging and statistical data analysis functions. Real-time and accumulated data may also be represented by a variety of measurement display configurations. The preferred configuration comprises a high-voltage supply 402 to power the detector 450, an electrometer/amplifier 404, data acquisition/signal processing 406, integration/averaging electronics 408, recorder/display 410 and a high voltage RF/AC power supply 412 to power the excimer lamp 100.

Figure 4:
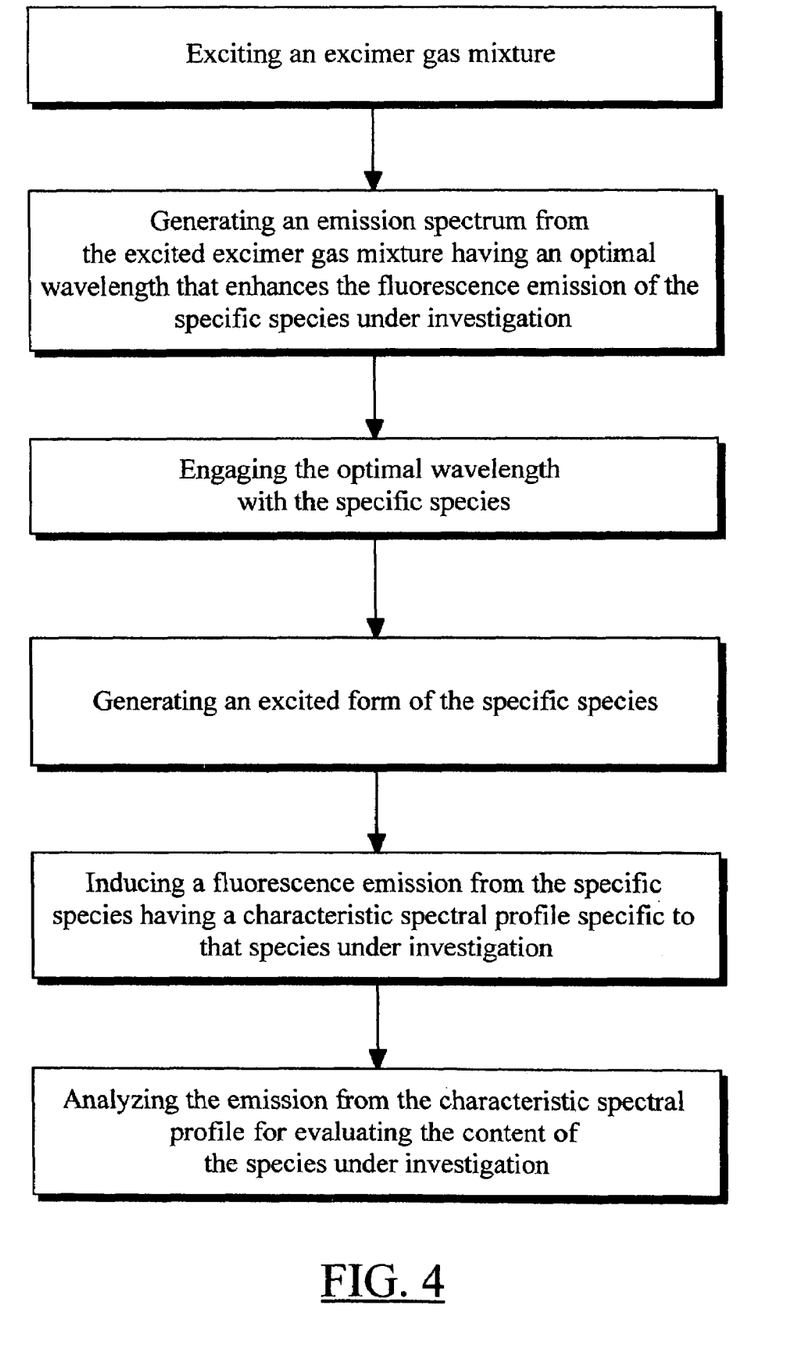
FIG. 4 is a flow chart illustrating a preferred UV fluorescence detection method of the present invention.

FIG. 4 is a flow chart illustrating a preferred UV fluorescence detection method of the present invention. The UV fluorescence detection method for detecting a specific species comprises the steps of exciting an excimer gas mixture, generating an emission spectrum from the excited excimer gas mixture having an optimal wavelength that enhances the fluorescence emission of the specific species under investigation, engaging the optimal wavelength with the specific species, generating an excited form of the specific species, inducing a fluorescence emission from the specific species having a characteristic spectral profile specific to that species under investigation, and analyzing the emission from the characteristic spectral profile for evaluating the content of species under investigation.

Figure 5:
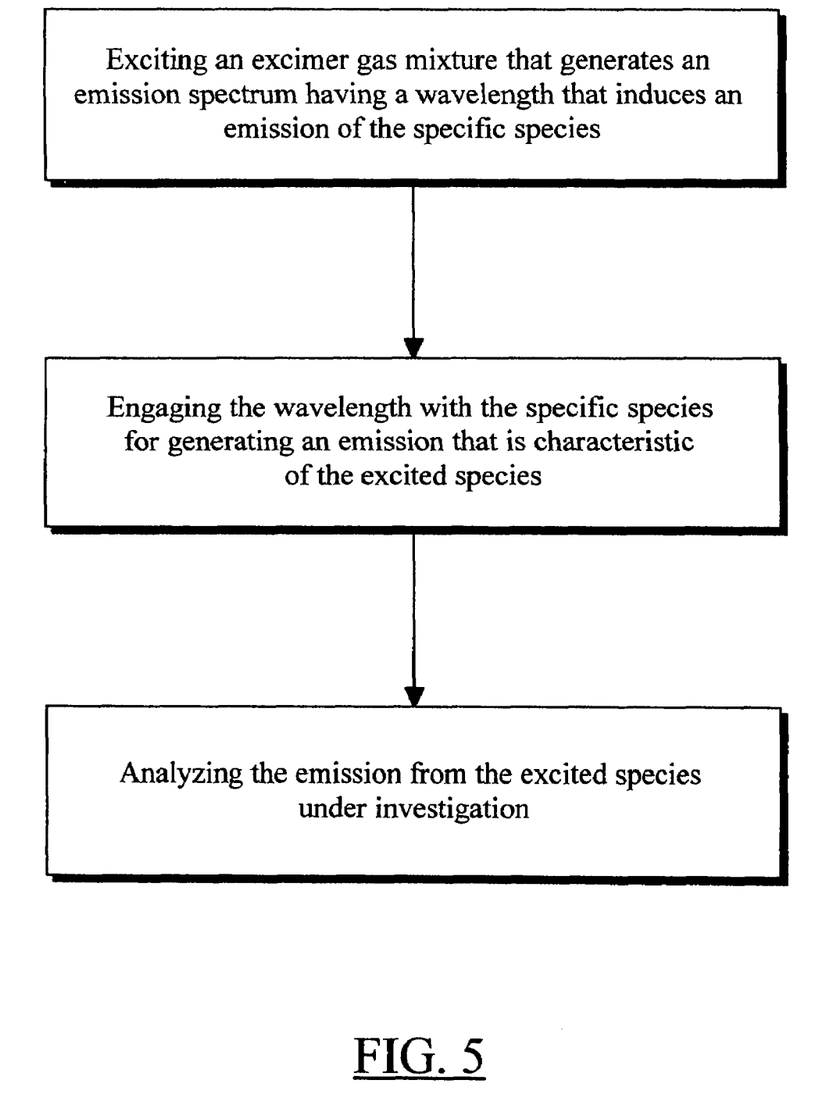
FIG. 5 is a flow chart illustrating another preferred UV fluorescence detection method of the present invention.

FIG. 5 is a flow chart illustrating another preferred UV fluorescence detection method of the present invention. The other preferred UV fluorescence detection method for detecting a specific species comprises the steps of exciting an excimer gas mixture that generates an emission spectrum having a wavelength that induces an emission of the specific species, engaging the wavelength with the specific species for generating a fluorescence emission that is characteristic of the excited species, analyzing the emission from the excited species under investigation.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A system for measuring the amount of sulfur in a sample comprising:
    (a) a UV fluorescence detector for determining the sulfur dioxide content of the sample comprising:
        (1) an excimer lamp comprising a quartz envelope and a krypton-chloride excimer gas mixture therein; the quartz envelope comprising:
            (A) an exterior cylindrical portion having an exterior cylindrical surface and an interior cylindrical surface,
            (B) an interior cylindrical portion having an interior cylindrical surface and an exterior cylindrical surface,
            (C) an emission aperture at a remote end of the quartz envelope in sealed association with the exterior cylindrical portion and the interior cylindrical portion, the emission aperture is substantially perpendicular to the longitudinal axis of the quartz envelope for transmitting photons there through, such that the interior cylindrical surface of the exterior cylindrical portion, the exterior cylindrical surface of the interior cylindrical portion and the emission aperture define a chamber for containing the krypton-chloride excimer gas mixture,
            (D) an inner electrode comprising a conductive solid metallic rod having effective contact with the interior cylindrical surface of the quartz envelope, and
            (E) an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode,
        (2) an excitation source comprising the quartz envelope;
        (3) a fluorescence chamber for housing a sample of gas containing sulfur dioxide such that the excitation source is in communication with the chamber;
        (4) a light sensitive detector in operative association with the fluorescence chamber; and
        (5) a device in communication with the light sensitive detector for determining the sulfur dioxide content of the sample in the fluorescence chamber, and
    (b) an analyzer for receiving the sulfur dioxide content of the sample from the UV fluorescence detector, the analyzer for evaluating the content of species under investigation and for quantifying the sulfur content in the sample.

2. The system for measuring the amount of sulfur in a sample as defined in claim 1 wherein the outer electrode comprises a first member and a second member symmetrically divided along the longitudinal axis of the quartz envelope, such that when the two members are joined together to encapsulate and hold the quartz envelope there between and having an interior diameter closely coinciding with the outer diameter of the quartz envelope.

3. The system for measuring the amount of sulfur in a sample as defined in claim 1 wherein the fluorescence chamber for housing a sample of gas containing sulfur dioxide further comprises an excitation source filter.

4. A UV fluorescence method for determining the sulfur dioxide content of a sample comprising the steps of:
    (a) detecting the sulfur dioxide content in the sample by exciting an excimer gas mixture within an excimer lamp; the excimer lamp comprising:
        (1) a quartz envelope, the quartz envelope comprising:
            (A) an exterior cylindrical portion having an exterior and interior cylindrical surface,
            (B) an interior cylindrical portion having an interior and exterior cylindrical surface,
            (C) an emission aperture at a remote end of the quartz envelope in operative association with the exterior cylindrical portion and the interior cylindrical portion, the emission aperture for transmitting photons there through, such that the interior cylindrical surface of the exterior cylindrical portion, the exterior cylindrical surface of the interior cylindrical portion and the emission aperture define a chamber for containing the excimer gas mixture,
            (D) an inner electrode comprising a conductive solid metallic rod having effective contact with the interior cylindrical surface of the quartz envelope, and
            (E) an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode;

(b) generating an emission spectrum by exciting the excimer gas mixture thereby, (c) creating an optimal wavelength that enhances the fluorescence emission of sulfur dioxide;

(d) engaging the optimal wavelength with sulfur dioxide;

(e) generating an excited form of sulfur dioxide;

(f) inducing a fluorescence emission from the excited form of sulfur dioxide having a characteristic spectral profile specific to sulfur dioxide, and (g) analyzing the emission from the characteristic spectral profile for evaluating the content of species under investigation and for quantifying the sulfur content in the sample.

5. The UV fluorescence method for determining the sulfur dioxide content of a sample as defined in claim 4 wherein the outer electrode comprises a first member and a second member symmetrically divided along the longitudinal axis of the quartz envelope, such that when the two members are joined together to encapsulate and hold the quartz envelope there between and having an interior diameter closely coinciding with the outer diameter of the quartz envelope.

6. A UV fluorescence detection system for determining the content of a sample having a specific gaseous species comprising:

(a) a dielectric barrier-discharge excimer lamp comprising a quartz envelope having an excimer gas mixture therein; the quartz envelope comprising:

(1) an exterior cylindrical portion having an exterior cylindrical surface and an interior cylindrical surface, (2) an interior cylindrical portion having an interior cylindrical surface and an exterior cylindrical surface, (3) an emission aperture at a remote end of the quartz envelope in sealed association with the exterior cylindrical portion and the interior cylindrical portion, the emission aperture is substantially perpendicular to the longitudinal axis of the quartz envelope for transmitting photons there through, such that the interior cylindrical surface of the exterior cylindrical portion, the exterior cylindrical surface of the interior cylindrical portion and the emission aperture define a chamber for containing the krypton-chloride excimer gas mixture, (4) an inner electrode comprising a conductive solid metallic rod having effective contact with the interior cylindrical surface of the quartz envelope, and (5) an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode, (b) a fluorescence chamber for housing a sample of gas containing the specific species of gas desired for measurement, the fluorescence chamber having an excitation filter such that the lamp is in communication with the fluorescence chamber;

(c) a light sensitive detector in operative association with the fluorescence filter of the fluorescence chamber; and (d) a device in communication with the light sensitive detector for determining the content of the specific species desired for measurement in the fluorescence chamber.

7. A UV fluorescence detection method for detecting a specific species comprising the steps of:

(a) exciting an excimer gas mixture within an excimer lamp comprising a quartz envelope, the quartz envelope comprising:

(1) an exterior cylindrical portion having an exterior and interior cylindrical surface, (2) an interior cylindrical portion having an interior and exterior cylindrical surface, (3) an emission aperture at a remote end of the quartz envelope in operative association with the exterior cylindrical portion and the interior cylindrical portion, the emission aperture for transmitting photons there through, such that the interior cylindrical surface of the exterior cylindrical portion, the exterior cylindrical surface of the interior cylindrical portion and the emission aperture define a chamber for containing the excimer gas mixture, (4) an inner electrode comprising a conductive solid metallic rod having effective contact with the interior cylindrical surface of the quartz envelope, and (5) an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode;

(b) generating an emission spectrum from the excited excimer gas mixture having a wavelength that enhances the fluorescence emission of the specific species under investigation;

(c) engaging the optimal wavelength with the specific species;

(d) generating an excited form of the specific species;

(e) inducing a fluorescence emission from the specific species having a characteristic spectral profile specific to that species under investigation, and (f) analyzing the characteristic spectral profile emission for evaluating the content of species under investigation.

8. A UV fluorescence detection method for detecting a specific species comprising the steps of:

(a) exciting an excimer gas mixture that generates an emission spectrum having an optimal wavelength that induces an emission of the specific species, the excimer gas mixture being excited in a quartz envelope, the quartz envelope comprising:

(1) an exterior cylindrical portion having an exterior and interior cylindrical surface, (2) an interior cylindrical portion having an interior and exterior cylindrical surface, (3) an emission aperture at a remote end of the quartz envelope in operative association with the exterior cylindrical portion and the interior cylindrical portion, the emission aperture for transmitting photons there through, such that the interior cylindrical surface of the exterior cylindrical portion, the exterior cylindrical surface of the interior cylindrical portion and the emission aperture define a chamber for containing the excimer gas mixture, (4) an inner electrode comprising a conductive solid metallic rod having effective contact with the interior cylindrical surface of the quartz envelope, and (5) an outer electrode comprising a conductive solid metallic housing having effective contact between the outer electrode and the exterior cylindrical surface of the quartz envelope, such that the quartz envelope is bounded on the interior cylindrical surface by the inner electrode and on the exterior cylindrical surface by the outer electrode;

(b) engaging the optimal wavelength with the specific species for generating an emission that is characteristic of the excited species;

(c) analyzing the emission from the excited species under investigation.

\* \* \* \* \*